(12) United States Patent
Kamiya et al.

(10) Patent No.: US 6,898,976 B2
(45) Date of Patent: May 31, 2005

(54) BRAKE NOISE DETECTION DEVICE

(75) Inventors: Masahiko Kamiya, Anjo (JP); Hiroshi Kondo, Chiryu (JP); Shin Sasaki, Okazaki (JP); Daizo Oba, Kariya (JP)

(73) Assignee: Advics Co., Ltd., Aichi-pref. (JP)

(*) Notice: Subject to any disclaimer, the term of this patent is extended or adjusted under 35 U.S.C. 154(b) by 0 days.

(21) Appl. No.: 10/779,618

(22) Filed: Feb. 18, 2004

(65) Prior Publication Data

US 2004/0187581 A1 Sep. 30, 2004

(30) Foreign Application Priority Data

Mar. 24, 2003 (JP) .......................... 2003-079685

(51) Int. Cl.$^7$ .............................. G01N 29/04
(52) U.S. Cl. ...................... 73/593; 73/659; 73/660
(58) Field of Search ................... 73/593, 579, 597, 73/600, 602, 659, 660

(56) References Cited

U.S. PATENT DOCUMENTS

| | | | | |
|---|---|---|---|---|
| 4,028,686 A | * | 6/1977 | Wilson et al. | 340/870.31 |
| 4,720,794 A | * | 1/1988 | Skarvada | 701/74 |
| 4,724,935 A | * | 2/1988 | Roper et al. | 188/181 R |
| 5,728,938 A | * | 3/1998 | Choi et al. | 73/593 |
| 5,948,961 A | * | 9/1999 | Asano et al. | 73/9 |
| 6,254,204 B1 | * | 7/2001 | Hara et al. | 303/183 |
| 6,264,292 B1 | * | 7/2001 | Umeno et al. | 303/196 |
| 6,687,644 B1 | * | 2/2004 | Zinke et al. | 702/145 |

FOREIGN PATENT DOCUMENTS

JP  A-2000-283193  10/2000

\* cited by examiner

*Primary Examiner*—Hezron Williams
*Assistant Examiner*—Jacques M. Saint-Surin
(74) *Attorney, Agent, or Firm*—Posz Law Group, PLC (57) ABSTRACT

An output signal that accords with a rotation speed of a brake rotor of a respective wheel is output by a vehicle wheel speed sensor. A noise frequency identification portion identifies a frequency component that corresponds to brake noise from this output signal. It is possible, for example, to identify a frequency component that corresponds to brake squeal by performing fast Fourier transform (FFT) calculation for the vehicle wheel speed. Further, a noise detection portion determines that brake noise is being generated when the frequency component identified by the noise frequency identification portion is equal to or more than a predetermined value.

10 Claims, 5 Drawing Sheets

BRAKE NOISE DETECTION DEVICE

CROSS REFERENCE TO RELATED APPLICATION

This application is based upon and claims the benefit of Japanese Patent Application No. 2003-079685 filed on Mar. 24, 2003, the content of which are incorporated herein by reference.

FIELD OF THE INVENTION

The present invention relates to a brake noise detection device.

BACKGROUND OF THE INVENTION

Conventional art is known for detecting generation of brake noise, such as brake squeal (for example, Japanese Patent Laid-Open Publication No. 2000-28319). In such art, a vibration frequency of at least one of a brake torque and a caliper pressing force is detected, and then it is determined that shudder is being caused when this vibration frequency is proportional to vehicle speed.

However, with this related art, it is necessary to specially provide a load sensor that detects brake load or a torque sensor that detects the brake torque within the caliper in order to detect the brake torque or the caliper pressing force. Accordingly, such art is both complicated and expensive.

SUMMARY OF THE INVENTION

In light of the above described problems, it is an object of the present invention to detect brake noise using a simple structure that does not require specialist sensors like vibration sensors to be provided.

In order to accomplish the above object, a brake noise detection device according to a first aspect of the present invention is provided with a vehicle wheel speed sensor that outputs an output signal in accordance with a rotation speed of a vehicle wheel; a noise frequency identification portion for identifying a frequency component that corresponds to brake noise based on the output signal of the vehicle wheel speed sensor; and a noise detection portion for determining that brake noise is being generated when the frequency component identified by the noise frequency identification portion is equal to or more than a predetermined value.

According to the first aspect of the present invention, when the frequency component included within the output signal of the vehicle wheel speed sensor that corresponds to brake noise is equal to or more than the predetermined value, it is determined that brake noise is being generated. Accordingly, it is possible to easily detect brake noise using the vehicle wheel speed sensor that is included in a normal brake apparatus, without having to provide a special sensor.

The first aspect may also be configured such that the vehicle wheel speed sensor includes a detected portion configured from a plurality of detected bodies which are disposed on at least one of an external circumference surface and a rotating surface of a rotating body that rotates integrally with the vehicle wheel, these detected bodies being disposed at equal distances apart in a circumferential direction of the rotating body; and a detection portion that is disposed so as to face the detected portion with a distance of separation. Further, the detection portion may output a signal in accordance with a relative movement speed of the detected portion and the detection portion.

In other words, it is possible to dispose the detected bodies on the external circumference surface of the rotating body or the rotating surface of the rotating body, as with a normal brake apparatus. In particular, when the detected bodies are disposed on the rotating surface and, in accordance with this, the detection portion is disposed so as to face the detected bodies and be perpendicular to the rotating surface, it is possible to detect surface swing of the rotating body that accompanies the generation of brake noise, such as brake squeal, during braking. Accordingly, it is possible to reliably detect brake noise.

Moreover, the configuration of the present invention may be such that the plurality of detected bodies in the detected portion are provided as between five hundred to one thousand detected bodies that are disposed at equal distances of separation. The number of the detected bodies is set such that, at low vehicle speed when brake noise is easily generated, the output signal of the vehicle wheel speed sensor is within a frequency band that is substantially equal to the frequency of brake noise. Accordingly, it is possible to accurately identify a frequency signal that corresponds to brake noise.

Moreover, the configuration of the present invention may be such that the noise frequency identification portion includes a vehicle wheel speed calculation portion that calculates a rotation speed of the vehicle wheel based upon the output signal of the vehicle wheel speed sensor; and a frequency calculation portion that calculates a frequency spectrum of the vehicle wheel speed by performing fast Fourier transform for the calculated rotation speed of the vehicle wheel. Furthermore, the configuration may be such that the noise frequency identification portion includes a frequency spectrum calculation portion that performs fast Fourier transform of the output signal of the vehicle wheel speed sensor; and a portion that excludes the frequency component that corresponds to the vehicle wheel speed from an output of the frequency spectrum calculation portion.

Moreover, the configuration of the present invention may be such that the vehicle wheel speed sensor is disposed within a caliper.

According to the above described configuration of the present invention, the vehicle wheel speed sensor can estimate changes in positional displacement of a caliper case and a brake case. Accordingly, it is possible to detect vibration of the caliper that occurs when brake noise of the caliper is generated, without utilizing a vibration sensor.

BRIEF DESCRIPTION OF THE DRAWINGS

Other objects, features and advantages of the present invention will be understood more fully from the following detailed description made with reference to the accompanying drawings. In the drawings.

DETAILED DESCRIPTION OF THE PREFERRED EMBODIMENTS

The present invention will be described further with reference to various embodiments in the drawings.

First Embodiment

Figure 1:
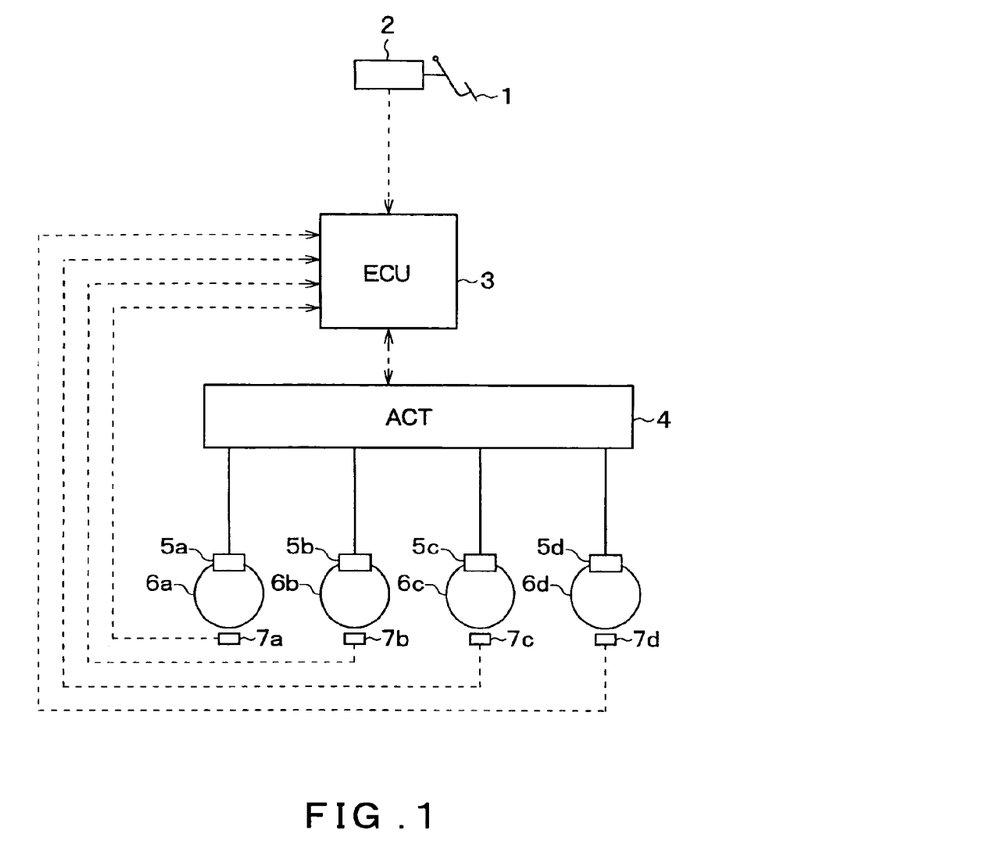
FIG. 1 is a schematic view showing a configuration of a first embodiment of the present invention.

Hereinafter, a first embodiment of a brake noise detection device according to the present invention will be explained with reference to the figures. FIG. 1 is a schematic view showing a configuration of the first embodiment.

As shown in FIG. 1, the brake noise detection device of the first embodiment is provided with a brake pedal 1 that is operated by a driver; a depression force sensor 2 that detects a pedal depression force as a depression state of the brake pedal 1; a electronic control unit (hereinafter referred to as "ECU") 3 configured from a computer that receives a detection signal from the depression force sensor 2; a drive unit 4 that is controlled by the ECU 3; and actuators (a brake force generation portion) 5a to 5d for brake actuation which are provided in each wheel 6a to 6d and which generate brake force for the respective vehicle wheels 6a to 6d, as a result of actuation of the drive unit 4.

The actuators 5a to 5d for brake actuation are configured from, for example, a motor, and a disk brake or a drum brake, or the like, that is driven by the motor. The drive unit 4, which is controlled by the ECU 3, executes adjustment of brake force by adjusting an amount of current fed to the motor. In addition, when an indicated current flows due to the drive unit 4, based on an instruction from the ECU 3, the actuators 5a to 5d for brake actuation generate brake force such that it is proportional to the indicated current.

Further, respective vehicle wheel speed sensors 7a to 7d that generate respective signals in accordance with rotation are provided in each of the wheels 6a to 6d. The vehicle wheel speed sensors 7a to 7d are connected to the ECU 3.

Figure 2:
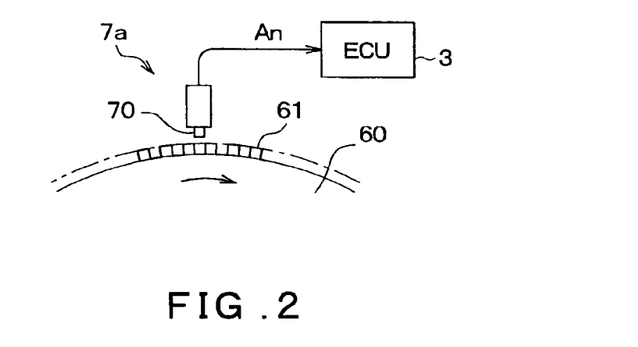
FIG. 2 is a schematic view showing a configuration of a vehicle wheel speed sensor.

Note that, FIG. 2 only shows, among the vehicle wheel speed sensors 7a to 7d, the vehicle wheel speed sensor 7a for the first wheel 6a. The vehicle wheel speed sensor 7a is configured from protruded and grooved teeth 61 and a magnetic pickup 70. The teeth 61, of which there are a predetermined number (from 500 to 1000), are formed at equal distances apart in a circumferential direction around an external periphery surface of a brake disk rotor 60, which acts as a rotating body for the respective wheel 6a. The teeth 61 are formed from a magnetic material such as steel and act as a detected body. The magnetic pickup 70 acts as a detection portion and is disposed so as to face the row of teeth 61 with a distance of separation.

Figure 3:
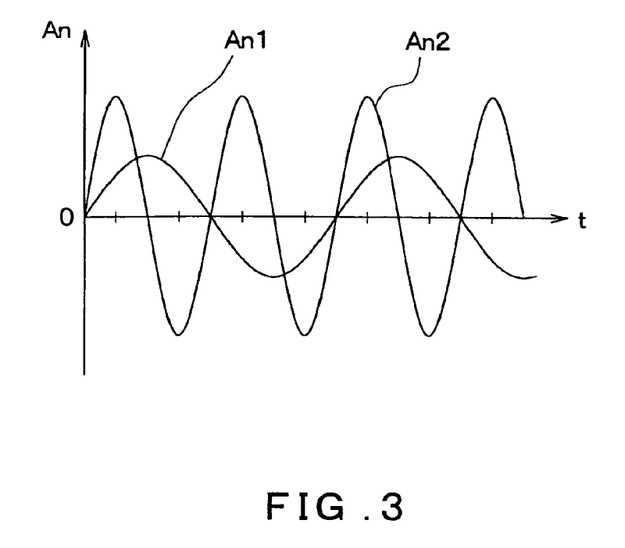
FIG. 3 is a chart showing an output waveform of the vehicle wheel speed sensor.
Figure 4:
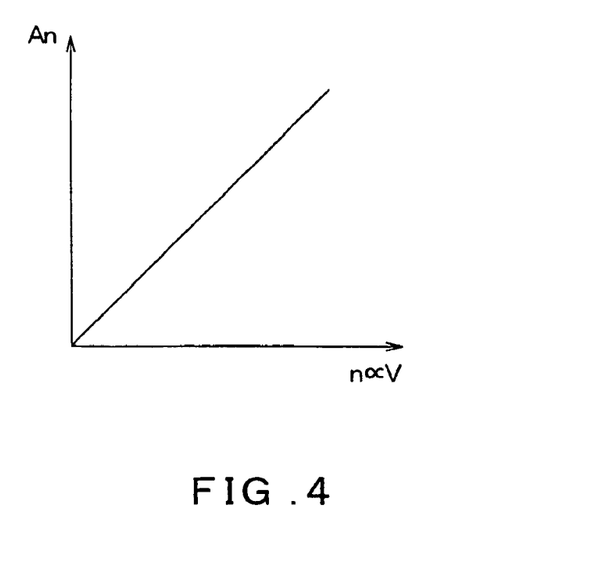
FIG. 4 is a chart showing a relationship between an output amplitude of the vehicle wheel speed sensor and a rotation speed.

Note that, the magnetic pickup 70 uses a known method in which an alternating current signal is generated by variation of magnetic flux that links with a coil (not shown) within the detection portion. The magnetic flux varies along with relative positional change of the magnetic pickup 70 with respect to the teeth 61 formed from steel or the like. Accordingly, due to the properties of the magnetic pickup 70, respective output signals of the vehicle wheel speed sensors 7a to 7d, as shown by the output waveform chart in FIG. 3, have a frequency and an amplitude An that become larger in accordance with a movement speed of the teeth 61 that are the detected body, namely, a rotation speed of the brake disk rotor 60. In FIG. 3, An1 and An2 indicate the respective output waveforms from the vehicle wheel speed sensors 7a to 7d at a low rotation speed and a high rotation speed, respectively. FIG. 4 shows the relationship between the amplitude An of the output signal and a rotation speed n. As is clearly apparent, the amplitude An has a proportional relationship to the rotation speed n, namely, a vehicle wheel speed V.

As an example, when a vehicle with 700 mm diameter tires is running at 20 km per hour, which is within a vehicle speed range at which brake noise is easily generated, the respective output signals of the vehicle speed sensors 7a to 7d are alternating current signals with a frequency of 2.53 kHz when the tooth number is 1000, and a frequency of 1.26 kHz when the tooth number is 500. Accordingly, the tooth number of the teeth 61 is appropriately selected from within a range from 500 to 1000. The frequency band of the output signal of the vehicle wheel speed sensors 7a to 7d is a frequency band with an order equal to 1 kHz to 5 to 6 kHz, which is the vibration frequency of brake noise. Thus, it is possible to accurately identify a signal that corresponds to brake noise from the output signal of the vehicle wheel speed sensors 7a to 7d.

Figure 5:
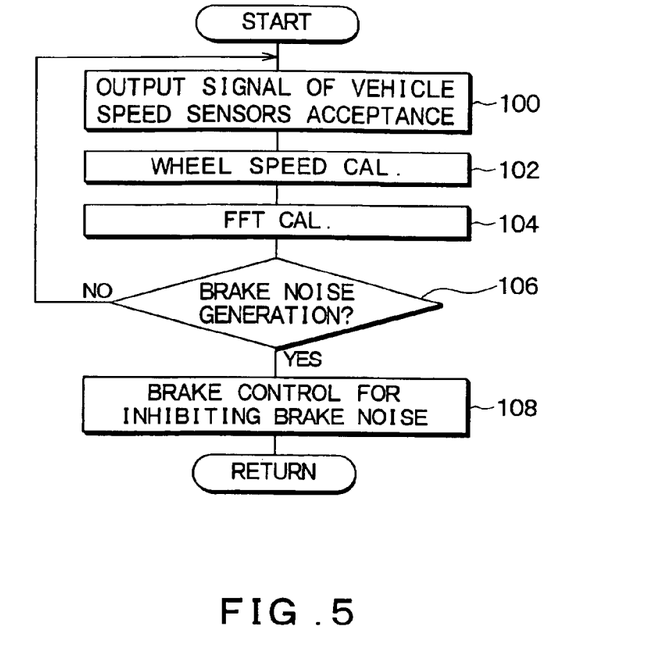
FIG. 5 is a flow chart showing a procedure for brake noise detection and inhibition processing that is executed by an ECU 3 of the first embodiment.

Next, the procedure of a brake noise detection processing that is executed by the ECU 3 of the first embodiment will be explained with reference to the flow chart of FIG. 5.

At 100, the output signal of the respective vehicle speed sensors 7a to 7d are accepted by the ECU 3. Next, at 102, waveform shaping of the alternating current signal that is output from the vehicle wheel speed sensors 7a to 7d (FIG. 3) is performed so as to execute conversion to a two value pulse signal. Along with this, an average value of the spacing between the two pulses is calculated at a predetermined sampling cycle, and the vehicle speed V is calculated from an inverse of the calculated average value. The calculated vehicle speed V is as shown in the time line graph of FIG. 6. More specifically, in the case that brake noise is not generated, the vehicle speed V is almost constant (V0 in FIG. 6) during a short time period interval. However, in the case that brake noise is generated, the vehicle speed V changes in response to generation of rotational variation in the vehicle wheel rotation in accordance with the frequency of the brake noise (V1 in FIG. 6).

Figure 6:
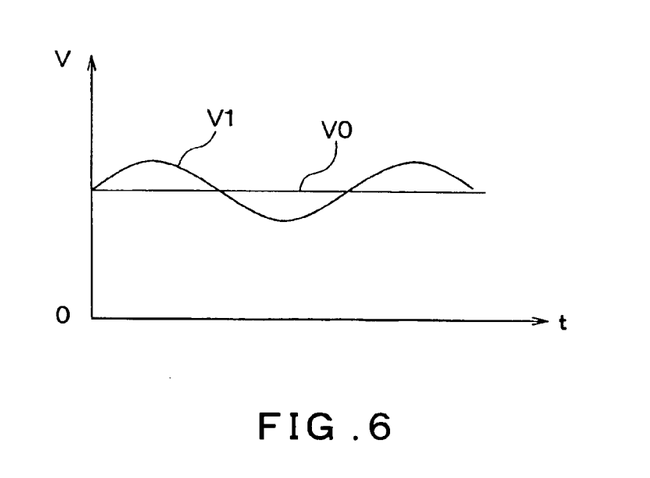
FIG. 6 is a graph showing a time waveform of a vehicle wheel speed.
Figure 7:
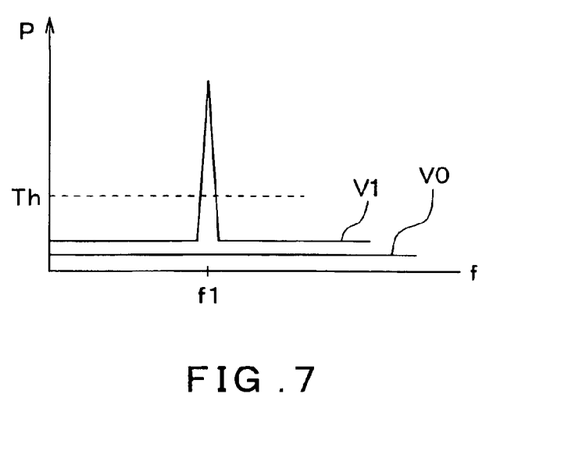
FIG. 7 is a diagram showing results attained by performing fast Fourier transform (FFT) calculation of variation of the vehicle speed.

At 104, fast Fourier transform (FFT) calculation is performed for the vehicle speed V shown in FIG. 6, and a frequency spectrum P of the vehicle speed V is calculated as shown in FIG. 7. This frequency spectrum P shows a gain peak at a frequency f1 that corresponds to the rotational variation of the brake disc rotor 60 in accordance with the brake noise. Accordingly, at 106, if the gain of the frequency spectrum P has become equal to or more than a predetermined value Th, it can be determined that brake noise, like brake squeal, is being generated. On the other hand, in the case that brake noise is not generated, a gain peak is not shown as indicated by V0 of FIG. 7, and thus the procedure returns to processing at 100.

Note that, within the ECU 3, a portion that executes the processing at 104 corresponds to a noise frequency identification portion, and a portion that executes the processing at 106 corresponds to a noise detection portion.

In the case that brake noise is being generated, a brake control for inhibiting brake noise is executed at 108. In particular, the drive device 4 executes a known brake control for inhibiting brake noise. More specifically, in this brake control, control is repeatedly executed in which, based on a control signal of the ECU 3, the brake force of the vehicle wheel that is generating brake noise is increased or decreased from a value determined based on the depression state of the brake pedal 1.

Second Embodiment

Hereinafter, a second embodiment will be explained. A brake noise detection device of the second embodiment differs from the above described first embodiment with respect to the processing that corresponds to the noise frequency identification portion. However, the schematic structural configuration of the second embodiment is the same as that shown in FIG. 1. Hereinbelow, an explanation will be given of the flow chart shown in FIG. 8, centering on those sections that are different from those of the first embodiment.

Figure 8:
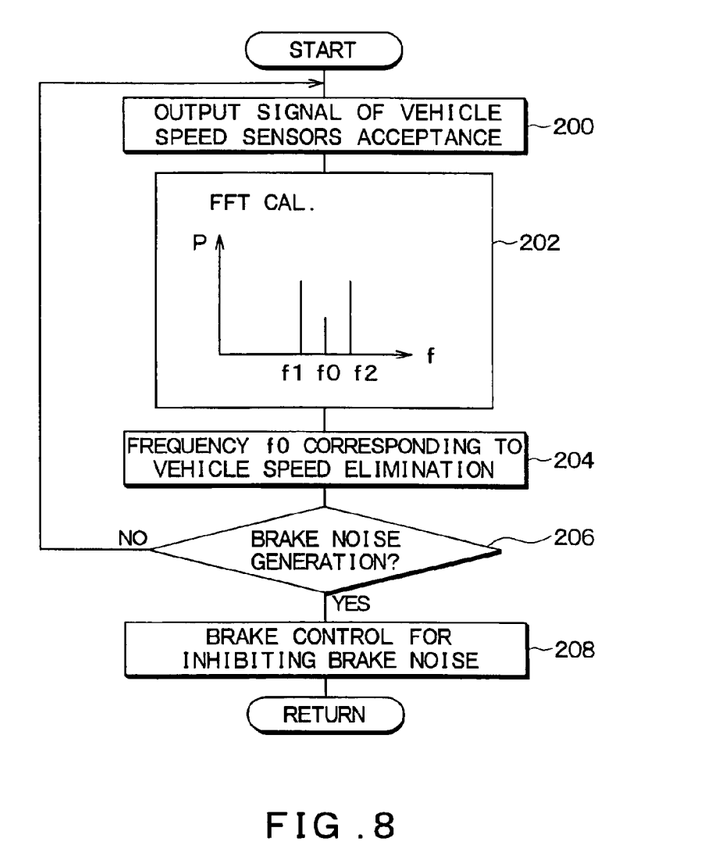
FIG. 8 is a flow chart showing a procedure for brake noise detection and inhibition processing that is executed by the ECU 3 of a second embodiment.

As shown in FIG. 8, at 200, the respective output signals from the vehicle wheel speed sensors 7a to 7d are accepted by the ECU 3. Next, at 202, FFT calculation is directly performed for the respective alternating current signals of the vehicle speed sensors 7a to 7d.

The respective output signals from the vehicle wheel speed sensors 7a to 7d when brake noise is being generated include a frequency f0 that corresponds to an almost constant vehicle speed; and, for example, two frequencies f1 and f2 (f1<f0<f2) that correspond to the rotational variation (increase or decrease of speed) that accompanies generation of the brake noise. Accordingly, when FFT calculation is performed for the respective sensor signals, the frequency spectrum P shows three peaks.

Therefore, at 204 in FIG. 8, the peak (frequency component) of the frequency f0 that corresponds to the vehicle speed which is constant is excluded from the frequency spectrum P, and then, at 206, it can be determined that brake noise is being generated if the respective gains of the frequencies f1 and f2 that correspond to the rotational variation are equal to or more than respective predetermined thresholds.

In the second embodiment, within the ECU 3, a portion that executes the processing at 202 and 204 corresponds to the noise frequency identification portion, and a portion that executes the processing at 206 corresponds to the noise detection portion.

In the case that brake noise is being generated, in a similar manner to the above described first embodiment, the brake control for inhibiting brake noise is executed at 208.

Third Embodiment

Hereinafter, a third embodiment will be explained. A brake noise detection device of the present embodiment differs from the brake noise detection device of the first and second embodiments with respect to the positioning method used for the vehicle wheel speed sensors.

Figure 9:
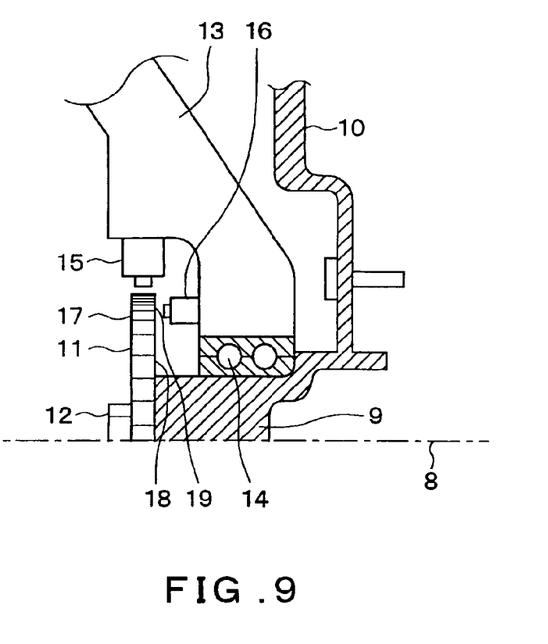
FIG. 9 is a schematic view showing the positioning of a vehicle wheel speed sensor in a third embodiment.

FIG. 9 is a cross sectional view showing the position of the vehicle wheel speed sensor of the third embodiment. Note that, FIG. 9 only shows an upper half of one vehicle axle 8. A hub shaft 9 provided with a brake disk 10 is supported by an axle bearing 13 via a bearing 14. A gear (rotor) 11, which acts as a detected portion, is fixed by a nut 12 to a shaft end of the hub shaft 9 so as to rotate integrally with a tire, not shown.

First teeth 17, which act as a detected body and of which there are a predetermined number (from 500 to 1000), are formed at equal distances apart in a circumferential direction around an external periphery surface of the gear 11. In addition, second teeth 19, of which there are the same number (500 to 1000) as the first teeth 17, are formed at equal distances apart in a circumferential direction on a rotating surface 18 of the teeth 11 (to the right side in FIG. 9).

A first detection portion (vehicle wheel speed sensor) 15 that faces the first teeth 17 at a distance of separation is fixed to an axle carrier 13, and a second detection portion (vehicle wheel speed sensor) 16 that faces the second teeth 19 at a distance of separation is also fixed to the axle carrier 13. The first and second detection portions (vehicle wheel speed sensors) 16 and 17 are both magnetic pickups, and are respectively connected to the ECU 3.

The ECU 3, in a similar manner to the first and second embodiments, acts as a noise frequency identification portion, and identifies the frequency components that correspond to brake noise from alternating current signals that are output from the respective vehicle wheel speed sensors 15 and 16 of each of the vehicle wheels 6a to 6d. It can be determined that brake noise is being generated when the identified frequency components are equal to or more than a predetermined value.

It should be noted that when brake noise is being generated, in the brake rotor that includes the brake disk 10, the gear 11, and the like, swing of the rotating surface 18 is simultaneously generated along with generation of variation in the rotation speed, as described above, in accordance with the brake noise.

With the third embodiment, a signal is generated by rotation of the second teeth 19 that are the detected body disposed on the rotating surface 18 of the gear (rotor) 11 detected by the second detection portion 16. This signal is output, in a similar manner to that of the first detection portion 15, as an alternating current signal having a frequency f0 that accords with the rotation speed of the rotor 11, namely, with the constant vehicle speed (a rotation speed of the tires) that is superimposed with frequencies f1, f2, and the like, that accord with rotational variation of the gear 11 that varies in accordance with brake noise. Further, an output signal from the second detection portion 16 is such that a variable signal that accords with the surface swing of the rotor 11 is superimposed on the variation in the rotation of the rotor 11 that accompanies the generation of brake noise. This signal results from the fact that the relative distance between the rotating surface 18 and the second detection portion 16 vary due to surface swing of the rotating surface 18, and thus an output voltage of the second detection portion 16 that accords with this distance variation changes to become comparatively larger. Accordingly, the variation frequency that accords with the surface swing is also equal to the frequency that corresponds to brake noise.

In this manner, according to the third embodiment, the second detection portion 16 detects the signal that accords with the surface swing of the rotor 11, and thus it is possible to reliably detect brake noise such as brake squeal.

Fourth Embodiment

Hereinafter, a fourth embodiment will be explained. In a brake noise detection device of the present embodiment as well, the positioning method for the vehicle wheel speed sensors differs from those of the brake noise detection device of the first and second embodiments.

Figure 10:
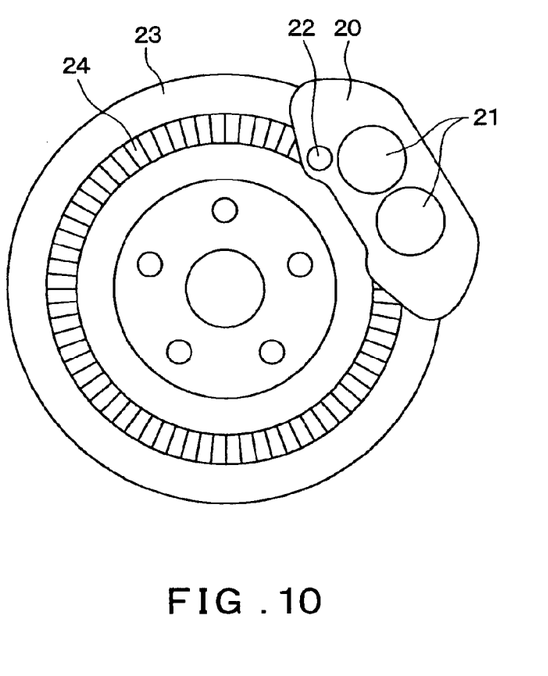
FIG. 10 is a schematic view showing the positioning of a vehicle wheel speed sensor in a fourth embodiment.

FIG. 10 shows the positioning of the vehicle wheel speed sensors of the fourth embodiment in a plan view of a brake disk 23 and a brake caliper 20 alone. Teeth 24, of which there are predetermined number (from 500 to 1000), are formed at equal distances apart at predetermined radial positions on a rotating surface of the brake disk 23. The teeth 24 act as a detected body.

On the other hand, a detection portion 22 that is a magnetic pickup is provided within the brake caliper 20 and positioned so as not to interfere with a brake piston 21 that pushes a friction member (not shown) against the brake disk 23. This detection portion 22 is positioned so as to face the teeth 24 at a distance of separation, and outputs an alternating current signal that accords with rotation of the brake disk 23 to the ECU 3.

As is known, when brake noise is generated during braking, coupled self-excited vibration of the brake disk 23 along with the friction member and the brake piston (not shown), and the like, is generated.

Accordingly, in the brake noise detection device of the present embodiment, the detection portion 22 positioned within the brake caliper 20 is able to detect not only the rotation speed of the brake disk 23, but also the variation in relative distance between the teeth 24 on the brake disk 23 and the brake caliper 20. Accordingly, it is possible to directly detect vibration (the variation in relative distance) of the brake caliper 20 that accompanies brake noise. For example, as one case of the generation of noise, even when just the brake caliper 20 vibrates while the brake disk 23 does not, it is possible to detect vibration of the brake caliper 20 using the detection portion 22 of the brake noise detection device of the present embodiment.

In this manner, according to the fourth embodiment, it is possible to detect vibration of the brake caliper 20, namely, the frequency signal of brake noise, using the detection portion 22 as a vehicle wheel speed sensor, without having to provide a special vibration sensor and reliably determine that brake noise is being generated.

Other Embodiments

In each of the above embodiments, examples were described in which a magnetic pickup was utilized as the vehicle wheel speed sensor. However, the present invention is not limited to this, and in particular, a speed sensor that utilizes a Hall device or a magnetic reluctance element, an optical pickup, or the like, may be utilized for detection of the rotation speed signal of the rotor.

Further, in each of the above embodiments, examples were described in which, as the noise frequency identification portion, FFT calculation is performed for the vehicle wheel speed variation or the magnetic pickup output. However, the present invention is not limited to this, and a band pass filter that identifies a signal of a frequency band that corresponds to brake noise may be adopted.

Moreover, in the first embodiment, the vehicle wheel speed V is calculated by calculation of the ECU 3. However, the vehicle wheel speed may be obtained as a voltage signal using a frequency-voltage (f-V) conversion circuit, or the like.

In addition, it is possible to configure the actuators 5a to 5d for brake actuation from a wheel cylinder that utilizes hydraulic fluid braking. In this case, the drive unit 4 can be an actuator provided with a master cylinder (not shown) that generates a master cylinder pressure due to depression of the brake pedal 1, a hydraulic circuit system that carries the master cylinder pressure to each wheel cylinder, and a normally open solenoid valve and a normally closed solenoid valve, or the like, that execute ABS control. Further, in this case, the ECU 3 can generate control signals for these solenoid valves.

While the above description is of the preferred embodiments of the present invention, it should be appreciated that the invention may be modified, altered, or varied without deviating from the scope and fair meaning of the following claims.

What is claimed is:

1. A brake noise detection device comprising:
    a vehicle wheel speed sensor that outputs an output signal in accordance with a rotation speed of a vehicle wheel;
    a noise frequency identification portion that identifies a frequency component that corresponds to brake noise based on the output signal of the vehicle wheel speed sensor; and
    a noise detection portion that determines that brake noise is being generated when the frequency component identified by the noise frequency identification portion is equal to or more than a predetermined value.

2. The brake noise detection device according to claim 1, wherein
    the vehicle wheel speed sensor includes a detected portion configured from a plurality of detected bodies which are disposed on at least one of an external circumference surface and a rotating surface of a rotating body that rotates integrally with the vehicle wheel, the detected bodies being disposed at equal distances apart in a circumferential direction of the rotating body; and
    a detection portion that is disposed so as to face the detected portion with a distance of separation, and
    the detection portion outputs a signal in accordance with a relative movement speed of the detected portion and the detection portion.

3. The brake noise detection device according to claim 2, wherein
    the plurality of detected bodies in the detected portion are provided as between five hundred to one thousand detected bodies that are disposed at equal distances of separation.

4. The brake noise detection device according to claim 3, wherein
    the noise frequency identification portion includes a vehicle wheel speed calculation portion which calculates a rotation speed of the vehicle wheel based upon the output signal of the vehicle wheel speed sensor, and which outputs a rotation speed signal based upon the calculated rotation speed; and a frequency calculation portion that calculates a frequency spectrum of the vehicle wheel speed by performing fast Fourier transform for the rotation speed signal of the vehicle wheel.

5. The brake noise detection device according to claim 3, wherein
    the noise frequency identification portion includes a frequency spectrum calculation portion that performs fast Fourier transform of the output signal of the vehicle wheel speed sensor; and a portion that excludes a frequency component that corresponds to the vehicle wheel speed from an output of the frequency spectrum calculation portion.

6. The brake noise detection device according to claim 2, wherein
    the noise frequency identification portion includes a vehicle wheel speed calculation portion which calculates a rotation speed of the vehicle wheel based upon the output signal of the vehicle wheel speed sensor, and which outputs a rotation speed signal based upon the calculated rotation speed; and a frequency calculation portion that calculates a frequency spectrum of the vehicle wheel speed by performing fast Fourier transform for the rotation speed signal of the vehicle wheel.

7. The brake noise detection device according to claim 2, wherein
    the noise frequency identification portion includes a frequency spectrum calculation portion that performs fast Fourier transform of the output signal of the vehicle wheel speed sensor; and a portion that excludes a frequency component that corresponds to the vehicle wheel speed from an output of the frequency spectrum calculation portion.

8. The brake noise detection device according to claim 1, wherein the noise frequency identification portion includes a vehicle wheel speed calculation portion which calculates a rotation speed of the vehicle wheel based upon the output signal of the vehicle wheel speed sensor, and which outputs a rotation speed signal based upon the calculated rotation speed; and a frequency calculation portion that calculates a frequency spectrum of the vehicle wheel speed by performing fast Fourier transform for the rotation speed signal of the vehicle wheel.

9. The brake noise detection device according to claim 1, wherein the noise frequency identification portion includes a frequency spectrum calculation portion that performs fast Fourier transform of the output signal of the vehicle wheel speed sensor; and a portion that excludes a frequency component that corresponds to the vehicle wheel speed from an output of the frequency spectrum calculation portion.

10. The brake noise detection device according to claim 1, wherein the vehicle wheel speed sensor is disposed within a caliper.

* * * * *